(12) United States Patent
Emelianov et al.

(10) Patent No.: US 8,904,871 B2
(45) Date of Patent: Dec. 9, 2014

(54) TEMPERATURE DEPENDENT PHOTOACOUSTIC IMAGING

(75) Inventors: Stanislav Emelianov, Austin, TX (US); Bo Wang, Austin, TX (US); Jignesh Shah, San Jose, CA (US); Konstantin Sokolov, Austin, TX (US); Jimmy Su, Austin, TX (US); Yun-Sheng Chen, Austin, TX (US); Wolfgang Frey, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 82 days.

(21) Appl. No.: 13/190,334

(22) Filed: Jul. 25, 2011

(65) Prior Publication Data
US 2012/0125107 A1    May 24, 2012

Related U.S. Application Data

(60) Provisional application No. 61/367,196, filed on Jul. 23, 2010.

(51) Int. Cl.
| | |
|---|---|
| *G01N 29/00* | (2006.01) |
| *G01N 21/00* | (2006.01) |
| *A61B 5/00* | (2006.01) |
| *A61B 5/02* | (2006.01) |
| *A61B 8/12* | (2006.01) |
| *A61B 6/00* | (2006.01) |
| *A61B 8/08* | (2006.01) |
| *G01N 21/17* | (2006.01) |

(52) U.S. Cl.
CPC ............ *A61B 8/5223* (2013.01); *A61B 5/0095* (2013.01); *A61B 6/481* (2013.01); *A61B 5/02007* (2013.01); *A61B 8/0891* (2013.01); *A61B 8/12* (2013.01); *G01N 21/1702* (2013.01)
USPC ................................................. 73/601; 73/643

(58) Field of Classification Search
USPC ........... 73/579, 649, 655, 656, 601, 602, 643, 73/606, 633
See application file for complete search history.

(56) References Cited

U.S. PATENT DOCUMENTS

| | | | | |
|---|---|---|---|---|
| 6,167,297 | A * | 12/2000 | Benaron | 600/431 |
| 6,216,540 | B1 * | 4/2001 | Nelson et al. | 73/633 |
| 6,246,901 | B1 * | 6/2001 | Benaron | 600/431 |
| 6,638,224 | B2 * | 10/2003 | Ohtsuki et al. | 600/443 |
| 7,668,587 | B2 * | 2/2010 | Benaron et al. | 600/476 |
| 8,364,414 | B2 * | 1/2013 | Masumura | 702/19 |
| 2005/0187471 | A1 * | 8/2005 | Kanayama et al. | 600/437 |
| 2006/0184042 | A1 * | 8/2006 | Wang et al. | 600/476 |

(Continued)

OTHER PUBLICATIONS

S. Sethuraman, et al., "Spectroscopic intravascular photoacoustic imaging to differentiate atherosclerotic plaques," *Optics Express*, vol. 16, pp. 3362-3367, 2008.
B. Wang, et al., "Detection of lipid in atherosclerotic vessels using ultrasound-guided spectroscopic intravascular photoacoustic imaging," *Opt. Express*, vol. 18, pp. 4889-4897, 2010.

(Continued)

*Primary Examiner* — Helen Kwok
(74) *Attorney, Agent, or Firm* — Baker Botts L.L.P.

(57) ABSTRACT

The present disclosure relates to methods and systems relating to temperature dependent photoacoustic imaging are provided. In such methods and systems, a tissue sample may be exposed to thermal energy and electromagnetic radiation to generate an acoustic signal, which may be detected. The amplitude of the acoustic signal may be determined and correlated with a tissue property, such as the presence or absence of macrophages or foam cells.

20 Claims, 7 Drawing Sheets

(56) References Cited

U.S. PATENT DOCUMENTS

| | | | |
|---|---|---|---|
| 2008/0014574 A1* | 1/2008 | Viator et al. | 435/4 |
| 2008/0154130 A1* | 6/2008 | Weiss et al. | 600/437 |
| 2009/0054763 A1* | 2/2009 | Wang et al. | 600/425 |
| 2009/0087493 A1* | 4/2009 | Dai et al. | 424/490 |
| 2009/0166560 A1* | 7/2009 | Dai et al. | 250/492.1 |
| 2009/0170149 A1* | 7/2009 | Viator et al. | 435/29 |
| 2010/0047356 A1* | 2/2010 | Yu et al. | 424/490 |
| 2010/0049044 A1* | 2/2010 | Burcher | 600/437 |
| 2010/0074845 A1* | 3/2010 | Gambhir et al. | 424/9.1 |
| 2011/0020239 A1* | 1/2011 | Bulte et al. | 424/9.6 |

OTHER PUBLICATIONS

B. Wang, et al., "Plasmonic Intravascular Photoacoustic Imaging for Detection of Macrophages in Atherosclerotic Plaques," Nano Lett, vol. 9, pp. 2212-2217, 2009.

Y.-S. Chen, et al., "Enhanced thermal stability of silica-coated gold nanorods for photoacoustic imaging and image-guided therapy," *Opt. Express,* vol. 18, pp. 8867-8878, 2010.

J. L.-S. Su, et al., "Photoacoustic imaging of coronary artery stents," Opt. Express, vol. 17, pp. 19894-19901, 2009.

J. Su, et al., "Photoacoustic imaging of clinical metal needles in tissue," Journal of Biomedical Optics, vol. 15, pp. 021309-6, 2010.

* cited by examiner (a)

(b)

TEMPERATURE DEPENDENT PHOTOACOUSTIC IMAGING

CROSS-REFERENCE TO RELATED APPLICATIONS

This application claims priority to U.S. Provisional Patent Application Ser. Nos. 61/367,196, filed Jul. 23, 2010, the entire disclosure of which is incorporated by reference.

STATEMENT OF GOVERNMENT INTEREST

This invention was made with government support under Grant Number HL084076 awarded by the National Institutes of Health. The government has certain rights in the invention.

BACKGROUND

Tissue characterization is of great interest in disease diagnosis and treatment. For example, in atherosclerosis, the composition of an atherosclerotic plaque is directly linked to the vulnerability of the plaque. Despite advances in determining risk factors and treating myocardial infarction, there are few techniques available for imaging the development and/or composition of atherosclerotic plaques, which play a major role in cardiovascular disease.

Macrophages are one of the key components involved in the pathology of atherosclerosis. At a relatively early stage in atherosclerotic development, macrophages are present at the "crime scene": macrophages are formed from the blood monocytes that enter the arterial wall because of the initial inflammation in the arterial endothelial layer. During the progression of the disease, lipid-laden macrophages play a partial role in the formation of atheroma. In particular, macrophages located in the arterial wall may accumulate low density lipoproteins (LDL) through endocytosis and form foam cells. Foam cells can form lipid pools under the endothelial layer of the arterial wall, which contributes greatly to the vulnerability of a plaque. Macrophage infiltration into the fibrous cap of plaques also accelerates disease progression by causing the release of matrix metalloproteinases (MMPs), which weaken the fibrous cap and make the plaques prone to rupture. Clearly, the distribution and activity of macrophages provide important information on the development of atherosclerotic plaques. Therefore, it is important to develop robust and cost-effective imaging methods sensitive to the cellular composition of plaques.

SUMMARY

The present disclosure generally relates to photoacoustic imaging. More particularly, the present disclosure relates to temperature dependent photoacoustic imaging.

In one embodiment, the present disclosure provides a method wherein a tissue sample is exposed to electromagnetic radiation and varying levels of thermal energy. Upon irradiation, the tissue sample generates acoustic signals, which are then detected using an ultrasonic sensor. The amplitudes of the detected acoustic signals are determined in relation to the varying levels of thermal energy, which may then be used to characterize the composition of the tissue sample. In some embodiments, the detected acoustic signals may be used to generate an image of the tissue sample. In some embodiments, a tissue sample may also comprise a contrast agent.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

Figure 3A:
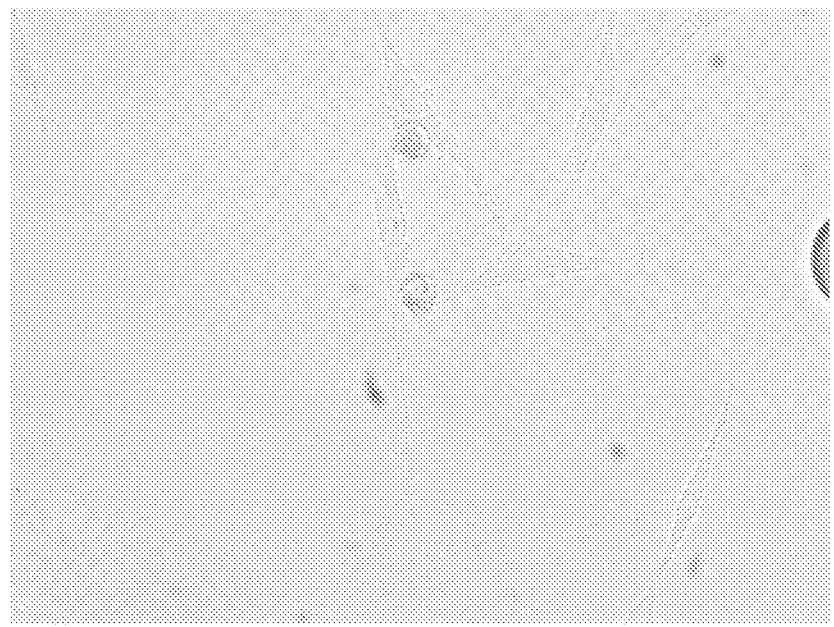
Figure 3B:
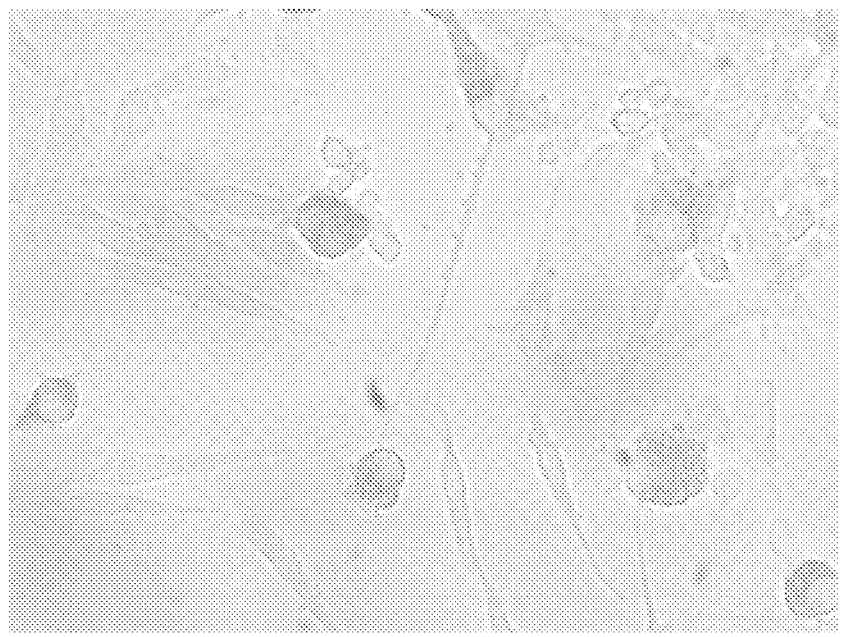
Figure 3C:
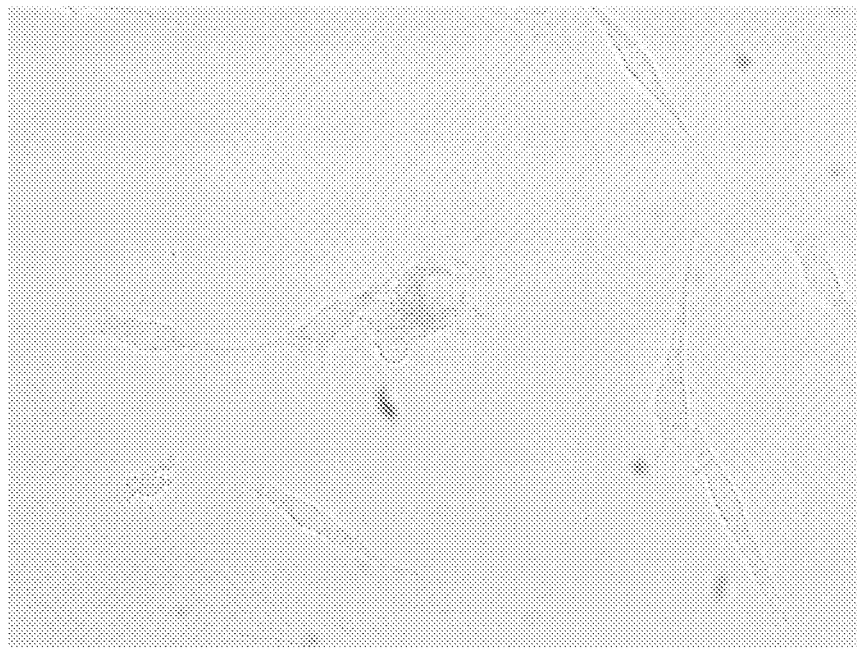
Figure 3D:
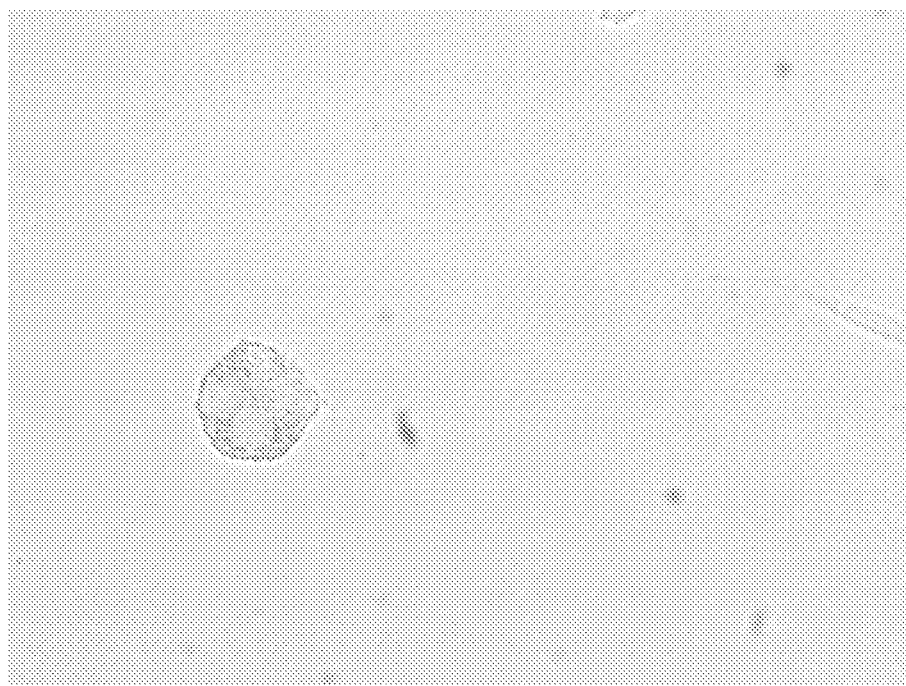

FIGS. 3A-3D show photoacoustic images of foam cells. FIGS. 3A and 3B are foam cells loaded with gold nanoparticles. The purple color in the cells in FIGS. 3A and 3B are from gold nanoparticles. FIGS. 3C and 3D are foam cells only.

Figure 4A:
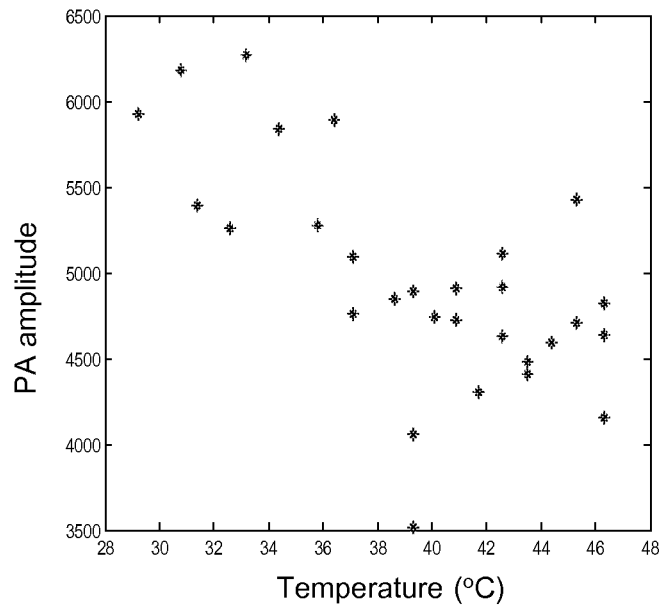
Figure 4B:
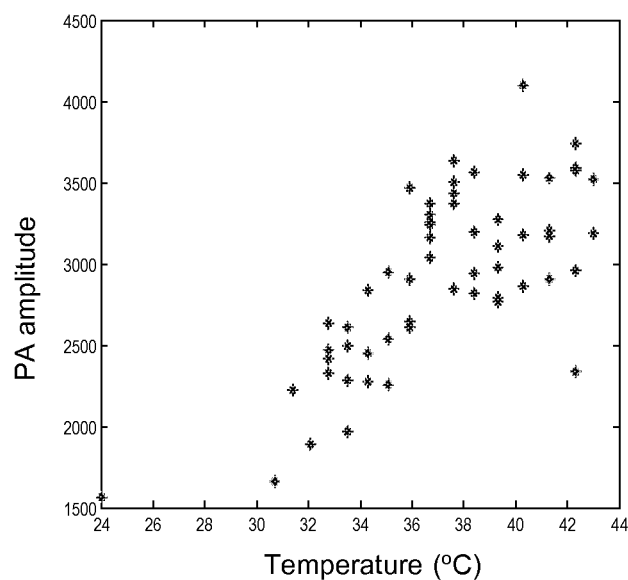

FIGS. 4A and 4B are graphs showing the photoacoustic signal amplitude versus temperature. FIG. 4A is a graph of the photoacoustic signal amplitude of spherical gold nanoparticles mixed with oxidized LDL. FIG. 4B is a graph of the photoacoustic signal amplitude of spherical gold nanoparticles in water. Experiments were performed at 532 nm wavelength.

Figure 5:
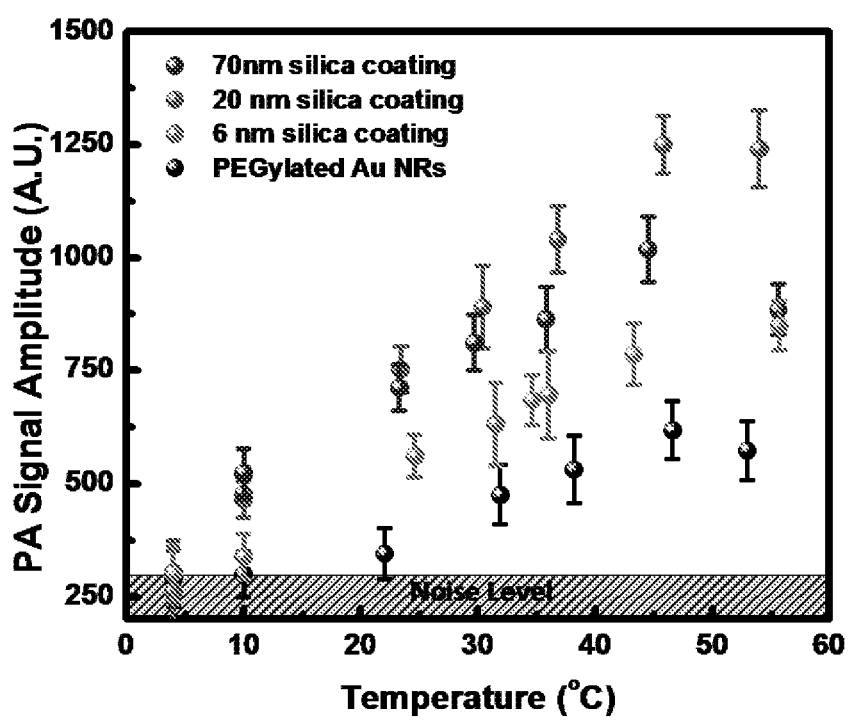

FIG. 5 is a graph showing the amplitude of photoacoustic signals generated from gold nanorods with various coatings.

Figure 6:
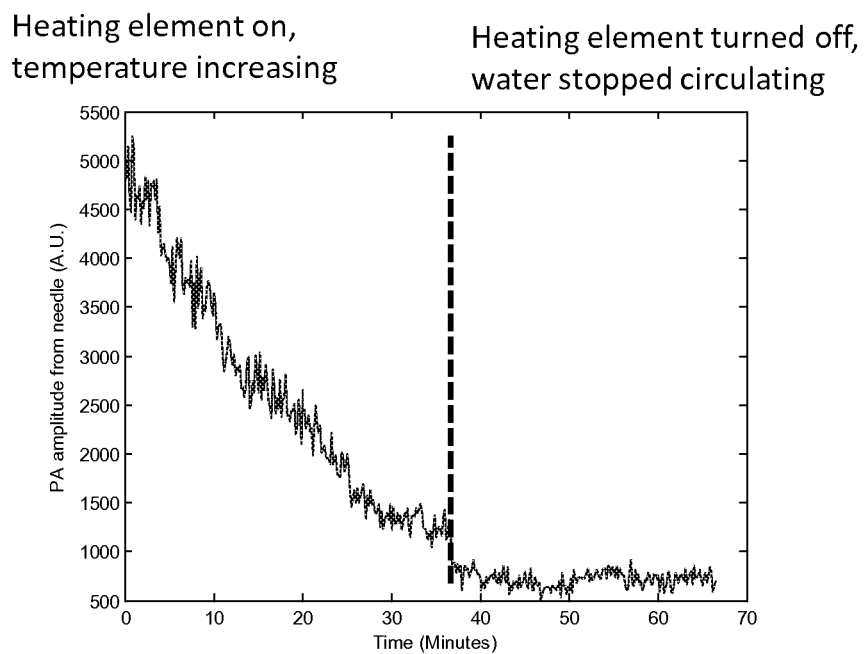

FIG. 6 is a graph showing the photoacoustic amplitude of a needle heated using a water bath where the temperature was increased for approximately 37 minutes. After this time, heating was turned off (indicated by dashed vertical line). Photoacoustic intensity remains stable for the remainder of the imaging time. Heating was delivered to the needle through electrodes connected to a DC power supply. Temperature change was estimated to be around +25° C. from room temperature.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to photoacoustic imaging. More particularly, the present disclosure relates to temperature dependent photoacoustic imaging.

In some embodiments, the methods of the present disclosure may allow for characterization of a tissue composition based on intrinsic properties, such as acoustic scattering, optical properties (optical scattering or absorption), and/or through introducing a contrast agent. The present disclosure is based, at least in part, on the fact that the amplitude of a photoacoustic signal is proportional to the fluence of the light, optical absorption coefficient of tissue, and a temperature dependent coefficient, known as the "Grüneisen coefficient." For different tissue types, the Grüneisen coefficient behaves differently with varying temperature. For example, the Grüneisen coefficient of water increases linearly with increased temperature, while the Grüneisen coefficient of fat decreases with increased temperature. Therefore, the present disclosure provides methods wherein the composition of a tissue sample may be detected by monitoring the amplitude of an acoustic signal under varying temperatures and in some embodiments, correlating an amplitude measurement to a Grüneisen coefficient.

Accordingly, in one embodiment, the present disclosure provides a method comprising exposing a tissue sample to thermal energy and electromagnetic radiation so as to generate an acoustic signal. The amplitude of the generated acoustic signal is determined, which may then be used, along with the correlated temperature, to provide information about the composition of the tissue sample. In particular, in some embodiments, the methods of the present disclosure may be used to detect the activity and/or location of macrophages and/or foam cells in a plaque. The methods of the present disclosure may further comprise subjecting the tissue sample to varying levels of thermal energy while maintaining the same wavelength of radiation. By monitoring photoacoustic signal amplitude changes relative to temperature, characteristics of a tissue sample may be determined. Similarly, the methods of the present disclosure may also allow for the identification of vulnerable plaques, which may be used to guide invasive treatments, such as stent deployment.

As mentioned above, the methods of the present disclosure comprise exposing a tissue sample to electromagnetic radiation. Examples of suitable sources of electromagnetic radiation may include, but are not limited to, a light source such as a laser, including a tunable pulsed laser or a fixed frequency pulsed laser. In some embodiments, a tissue sample may be exposed to pulses of irradiation with a duration of about 1 nanoseconds ("ns") to about 1000 ns. When the tissue to be imaged is simulated by a solid slab tissue, the radiation fluence on the surface of the slab will be about 10 mJ/cm$^2$. For other configurations of the test sample, or for living human or non-human bodies the surface fluence will vary, but will always be in a range which is generally considered safe according to the ANSI laser operation standards.

In accordance with the present disclosure, a wavelength of electromagnetic radiation may be chosen to match the type of tissue being imaged or, if a contrast agent is present in the tissue sample, based on the absorption of the contrast agent. For example, lipid has an optical absorption peak at approximately 1200 nm. One of ordinary skill in the art with the benefit of this disclosure will be able to select an appropriate wavelength based on the type of tissue sample being evaluated and/or the optical absorption spectra of the contrast agent present within the sample. Furthermore, in some embodiments, a tissue sample may be irradiated at only one wavelength. As a result of using the temperature dependent photoacoustic imaging methods of the present disclosure, the present disclosure may allow for characterization of a tissue sample without the need for multi-wavelength imaging, which may dramatically lower the cost and requirement of the electromagnetic radiation source.

In addition to electromagnetic radiation exposure, the methods of the present disclosure also comprise exposing a tissue sample to varying levels of thermal energy. Examples of suitable thermal energy sources may include any type of heating or cooling element, a heating or cooling water immersion element, etc.

The methods of the present disclosure generally contemplate irradiating a tissue sample at a first temperature and then irradiating the sample at a second increased temperature, however the methods of the present disclosure may also be practiced by irradiating a tissue sample at a first temperature and then irradiating the sample at a second decreased temperature. In some embodiments, the temperature may be varied by approximately 5° C. between measurements, although a difference of any amount is contemplated within this disclosure. Furthermore, in some embodiments, the temperature may vary from approximately 4 to 55° C. However, as would be recognized by someone of skill in the art, a temperature exceeding 40° C. would only be used in conjunction with photothermal therapy, as temperatures in excess of 40° C. generally damage tissue.

After irradiation, a generated acoustic wave may be detected using any suitable detection source including, but not limited to, an ultrasonic sensor. Example ultrasonic sensors may include, but are not limited to, transducers including piezoelectric films, such as polyvinylidene fluoride, optical transducers, and optical interferometers.

In some embodiments, a suitable electromagnetic source, a suitable thermal energy source, and a suitable detection source may be combined into one system, which may also be capable of generating an image based at least in part on the detected acoustic signals. Systems suitable for use in the present disclosure may comprise not only a suitable electromagnetic source, a suitable thermal energy source and a suitable detection source, but may also comprise additional electronic and mechanical components such as a pulser/receiver, a digitizer, a motion controller, a three-dimensional positioning stage, a stepper motor, a delay switch, a microprocessor or data acquisition unit, and/or a display monitor. One of ordinary skill in the art, with the benefit of this disclosure, will recognize additional electronic and mechanical components that may be suitable for use in the methods of the present disclosure. In some embodiments, photoacoustic imaging may be augmented by ultrasound imaging as these imaging systems are complementary. Indeed, photoacoustic imaging can generally be transparently integrated with ultrasound since both photoacoustic and ultrasound imaging systems can utilize the same ultrasound sensor and associated receiver electronics.

In one embodiment, the methods of the present disclosure may comprise using an intravascular photoacoustic (IVPA) imaging device, which may be a catheter-based imaging device. An IVPA imaging device may be particularly useful when imaging atherosclerosis. In particular, IVPA imaging has high spatial resolution and sufficient imaging depth for detecting atherosclerosis. Compared to noninvasive cardiovascular imaging modalities such as MRI and CT, IVPA imaging can achieve higher spatial resolution depending on the transducer frequency used in the application. Furthermore, as compared to invasive but high resolution imaging modalities such as OCT, IVPA has a larger penetration depth of several millimeters relative to 1-2 mm imaging depth in OCT. In addition, by choosing the imaging wavelengths in the near-infrared (NIR) range where the optical absorption of oxygenated and deoxygenated blood is low, IVPA imaging may be performed in the presence of luminal blood without the need to flush the vessel with saline.

Tissue samples suitable for use in the methods of the present disclosure may comprise any biological tissue. In some embodiments, a tissue sample suitable for use in the present disclosure may comprise one or more contrast agents or other foreign object. Contrast agents suitable for use in the present disclosure may include, but are not limited to, any metallic nanoparticle comprising a biocompatible metal that exhibits plasmon resonance. Examples of suitable biocompatible metals that exhibit plasmon resonance include, but are not limited to, copper and noble metals, such as gold and/or silver. In some embodiments, nanoparticles suitable for use may be coated to optimize their biological and chemical properties and/or to maximize the acoustic signal generated. Examples of suitable nanoparticles may include those described in U.S. Patent Publication No. 2005/0175540, which is hereby incorporated by reference in its entirety.

Additionally, in some embodiments of the present disclosure, suitable nanoparticles may also act as a targeted delivery system for therapeutic agents. In some embodiments, the targeting mechanism may be antibodies, foliates, aptamers, and/or polymers that are attached to the outside of the nanoparticles. For example, the targeting antibodies may be specific to upregulated receptors on the surface of cancerous cells. In some embodiments, the drug release may be optically triggered with the use of a laser.

To facilitate a better understanding of the present invention, the following examples of certain aspects of some embodiments are given. In no way should the following examples be read to limit, or define, the scope of the invention.

EXAMPLES

Figure 1A:
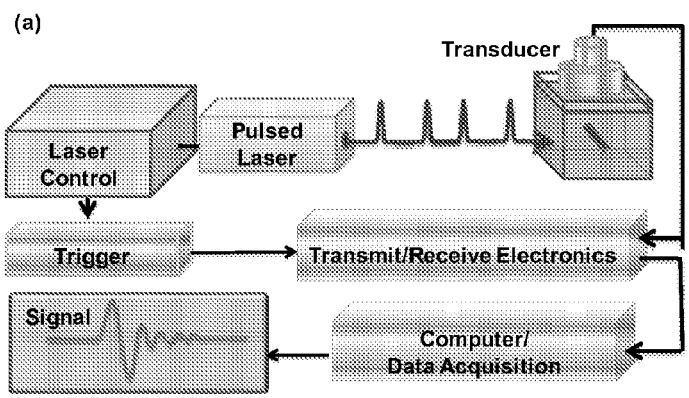
FIGS. 1A-1C depict a block diagram of an experimental setup for the characterization of the photoacoustic response of gold nanorods, according to one embodiment.

One example of a specific setup suitable for measuring the photoacoustic response from gold nanorods is schematically illustrated in FIG. 1A. A single element focused ultrasound transducer (7.5 MHz center frequency, 50.4 mm focal distance, and 13 mm aperture, Panametrics Inc., V320) was mounted on a one-dimensional positioning stage. Nanosecond laser pulses (7 ns pulse duration, 2 Hz repetition rate) uniformly irradiated the sample. For each laser pulse, the photoacoustic signal was captured and stored for off-line processing. The amplitude of the recorded photoacoustic signal from each pulse was first compensated for the pulse-to-pulse fluence fluctuation, then the photoacoustic signal of each pulse was normalized to the maximum photoacoustic signal recorded. For each sample, mean and standard deviation were computed using 60 photoacoustic signals. No systematic changes that would indicate a change in the nanorods was detected.

Figure 1B:
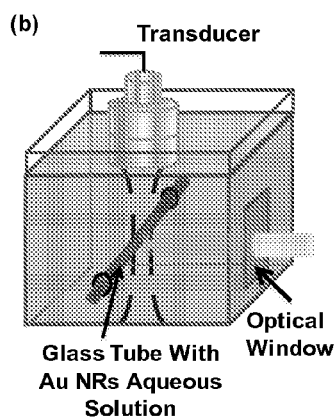

The photoacoustic responses from gold nanorods in water solution were characterized by using the setup shown in FIG. 1B. The extinction of each 100 μL gold nanorod solution in a standard 96-well plate was first adjusted to 1.5 using UV-Vis measurements. A 1 mm diameter glass tube was fixed in an acrylate water tank containing an optical window inlay. The glass tube contains an inlet and an outlet for injecting the 20 μL aliquot into the glass tube without moving the tube during the experiment. The position of the transducer was adjusted so that the injected solution within the tube was located in the center of the ultrasound beam, and the distance between the transducer and the glass tube was kept constant during the entire experiment. During the experiment the water temperature of the acrylate tank was controlled by a thermal circulator.

Figure 1C:
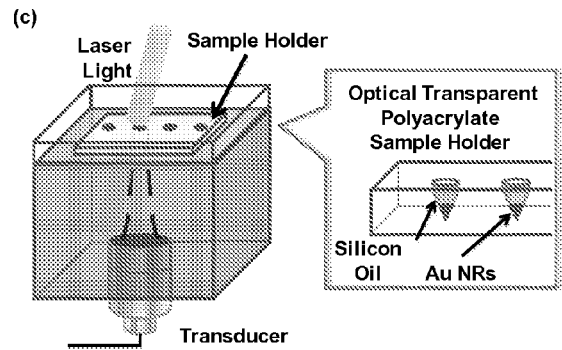

To exchange solvent from water to oil, 2 μL of the gold nanorods aqueous solution (O.D.=1.5) was added to a custom-made cone shape well drilled within the optically transparent acrylate plate. The plate was placed in a low-temperature vacuum oven to evaporate the solvent. This procedure was repeated twenty times until 20 μL aliquote of gold nanorods was added and solvent was evaporated. Thereafter, 20 μL of silicon oil was added to each well. The experimental setup to measure the photoacoustic response of the samples is shown schematically in FIG. 1C. The bottom of the sample plate was immersed in water to ensure good acoustic coupling and signal transmission. The collimated laser beam irradiated the sample from the top and the ultrasound transducer was placed below the plate near the bottom of the water tank. The position of the transducer was adjusted so that the sample was located at the intersection of laser and ultrasound beams and the distance between transducer and sample was kept constant during the entire experiment.

Figure 2:
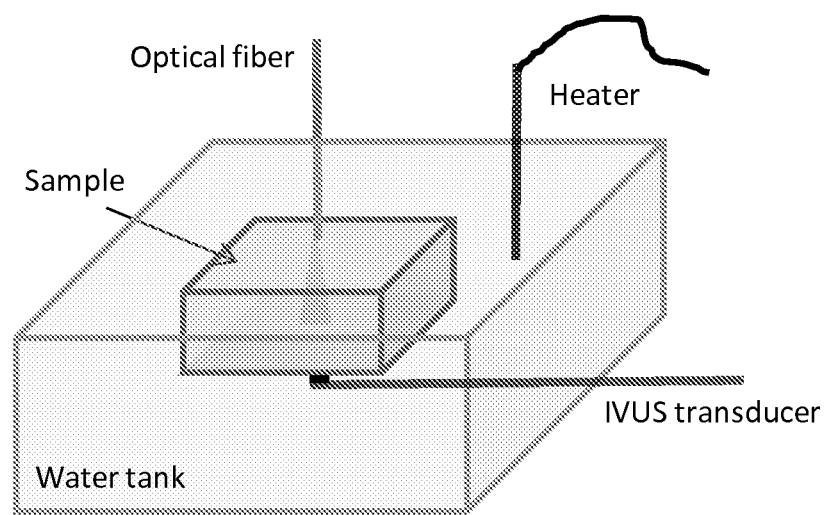
FIG. 2 depicts a schematic of an experimental setup for the characterization of the photoacoustic response of a sample, according to one embodiment.

Another example of a specific setup suitable for measuring the photoacoustic response from a sample is schematically illustrated in FIG. 2. Samples (oxLDL mixed with Au NPs or Au NPs in water) were placed in a cuvet which was immersed in a water tank. A heater was immersed in the water tank to increase the sample's temperature. To cool down the samples, ice was added to the water tank. Laser beam was directed through an optical fiber onto the sample. The bottom of the cuvet was made out of glass cover slip. A 40 MHz single element intravascular ultrasound (IVUS) transducer was placed under the cuvet, with the transducer element aligned with the laser beam. As the temperature of the samples was changed, photoacoustic signals generated by the sample were captured after each laser pulse using the IVUS transducer.

The results in FIG. 6 were obtained by heating a commercial off-the-shelf syringe needle (21G) in a water bath and monitoring continuously using photoacoustic imaging. Photoacoustic imaging was performed at 800 nm, at which the stainless steel metal of the needle has an absorption coefficient of approximately $10^4$ cm$^{-1}$. A 7.5 Mhz ultrasound array transducer was used to detect photoacoustic signals. One complete imaging plane was obtained every 10 seconds, and imaging was performed continuously over one hour. Images were reconstructed offline and the photoacoustic intensity of the needle was recorded in each image. At the 37 minute mark, the heat increase was stopped. Results showed that the photoacoustic intensity decreased with increasing temperature. When the temperature remained constant, the photoacoustic intensity also remained unchanged. Additional experiments were conducted in which the temperature was lowered over time, and demonstrated increasing photoacoustic intensity.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. S. Sethuraman, et al., "Spectroscopic intravascular photoacoustic imaging to differentiate atherosclerotic plaques," *Optics Express*, vol. 16, pp. 3362-3367, 2008.
2. B. Wang, et al., "Detection of lipid in atherosclerotic vessels using ultrasound-guided spectroscopic intravascular photoacoustic imaging," *Opt. Express*, vol. 18, pp. 4889-4897, 2010.
3. B. Wang, et al., "Plasmonic Intravascular Photoacoustic Imaging for Detection of Macrophages in Atherosclerotic Plaques," *Nano Lett*, vol. 9, pp. 2212-2217, 2009.
4. Y.-S. Chen, et al., "Enhanced thermal stability of silica-coated gold nanorods for photoacoustic imaging and image-guided therapy," *Opt. Express*, vol. 18, pp. 8867-8878, 2010.
5. J. L.-S. Su, et al. "Photoacoustic imaging of coronary artery stents," *Opt. Express*, vol. 17, pp. 19894-19901, 2009.
6. J. Su, et al., "Photoacoustic imaging of clinical metal needles in tissue," *Journal of Biomedical Optics*, vol. 15, pp. 021309-6, 2010.

What is claimed is:

1. A method of detecting a macrophage or foam cell in a tissue sample comprising:
   providing a contrast agent to a tissue sample, wherein the contrast agent comprises a metallic nanoparticles;
   exposing at least a portion of the tissue sample to a first level of thermal energy and to electromagnetic radiation and so as to generate a first acoustic signal;
   detecting the first acoustic signal;
   determining an amplitude of the first acoustic signal;
   exposing at least a portion of the tissue sample to a second level of thermal energy and to electromagnetic radiation so as to generate a second acoustic signal;
   detecting the second acoustic signal;
   determining the amplitude of the second acoustic signal; and
   correlating the amplitude of the first acoustic signal and the amplitude of the second acoustic signal with the presence or absence of a macrophage or foam cell in the tissue sample, wherein the acoustic signal amplitude change relative to level of thermal energy indicates the presence or absence of a macrophage or foam cell in the tissue sample.

2. The method of claim 1 wherein exposing the portion of the tissue sample to the first level of thermal energy and electromagnetic radiation occurs simultaneously.

3. The method of claim 1 further comprising:
   correlating the amplitudes of the first and second acoustic signals to a Grüneisen coefficient.

4. The method of claim 1 further comprising:
   generating an image of at least a portion of the tissue sample from the detected first acoustic signal and second acoustic signal.

5. The method of claim 1 wherein the tissue sample is only exposed to one wavelength of electromagnetic radiation.

6. The method of claim 1, wherein the metallic nanoparticles comprise copper.

7. The method of claim 1, wherein the metallic nanoparticles comprise a noble metal.

8. The method of claim 7, wherein the noble metal comprises gold.

9. The method of claim 7, wherein the noble metal comprises silver.

10. The method of claim 1, wherein the metallic nanoparticles comprises a silica coating.

11. The method of claim 1, wherein the tissue sample comprises an atherosclerotic plaque.

12. The method of claim 1, wherein the tissue sample comprises an artery.

13. The method of claim 1, wherein exposing at least a portion of the tissue sample to electromagnetic radiation comprises exposing at least a portion of the tissue sample to pulses of irradiation lasting from about 1 nanosecond to about 1000 nanoseconds.

14. The method of claim 1, wherein the electromagnetic radiation comprises one wavelength.

15. The method of claim 1, wherein the electromagnetic radiation comprises more than one wavelength.

16. The method of claim 1, wherein detecting the acoustic signal comprises detecting with an ultrasonic sensor.

17. The method of claim 1, wherein at least one of the exposing or detecting steps is performed by an intravascular photoacoustic imaging device.

18. The method of claim 1, wherein the first level of thermal energy and second level of thermal enemy are both sufficient to heat the tissue sample to no greater than 40° C.

19. The method of claim 1, wherein determining and correlating and performed by a microprocessor or a data acquisition unit.

20. The method of claim 1, further comprising:
   exposing at least a portion of the tissue sample to a plurality of additional levels of thermal energy and to electromagnetic radiation and so as to generate a plurality of additional acoustic signals;
   detecting the plurality of additional acoustic signals;
   determining an amplitude of the additional acoustic signals; and
   correlating the amplitude of the first acoustic signal, the amplitude of the second acoustic signal, and the amplitudes of the plurality of additional acoustic signals with the presence or absence of a macrophage or foam cell in the tissue sample.

* * * * *